United States Patent
Uchiyama

(10) Patent No.: US 9,134,274 B2
(45) Date of Patent: Sep. 15, 2015

(54) DISCHARGE IONIZATION CURRENT DETECTOR

(71) Applicant: SHIMADZU CORPORATION, Kyoto (JP)

(72) Inventor: Shinji Uchiyama, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 111 days.

(21) Appl. No.: 13/777,585

(22) Filed: Feb. 26, 2013

(65) Prior Publication Data

US 2013/0221972 A1  Aug. 29, 2013

(30) Foreign Application Priority Data

Feb. 28, 2012 (JP) .................................. 2012-041288

(51) Int. Cl.
 *G01N 27/62* (2006.01)
 *G01N 27/66* (2006.01)
(52) U.S. Cl.
 CPC ..................................... *G01N 27/66* (2013.01)
(58) Field of Classification Search
 CPC .. H01J 37/3244; H01J 37/32449; H01J 37/00
 See application file for complete search history.

(56) References Cited

U.S. PATENT DOCUMENTS

| 5,892,364 A | 4/1999 | Monagle |
| 8,114,181 B2 * | 2/2012 | Gogolin ..................... 55/385.1 |
| 2011/0187379 A1 * | 8/2011 | Shinada et al. ............... 324/464 |

FOREIGN PATENT DOCUMENTS

| JP | 51-83586 A | 7/1976 |
| JP | 2010-060354 A | 3/2010 |

OTHER PUBLICATIONS

Office Action dated Feb. 3, 2015, issued in corresponding Japanese application No. 2012-041288. (2 pages).

* cited by examiner

*Primary Examiner* — Tung X Nguyen
*Assistant Examiner* — Feba Pothen
(74) *Attorney, Agent, or Firm* — Westerman, Hattori, Daniels & Adrian, LLP

(57) ABSTRACT

A discharge ionization current detector is provided with a dielectric tube through which plasma generating gas flows, a plasma generating unit formed from one section of the dielectric tube in a flow direction of the plasma generating gas, a casing connected to a lower end portion, in the flow direction of the plasma generating gas, of the dielectric tube, a sample ionization unit provided inside the casing, and an ion current detection unit for detecting a sample component ionized by the sample ionization unit. The lower end, in the flow direction of the plasma generating gas, of the dielectric tube protrudes into the space inside the casing.

4 Claims, 3 Drawing Sheets

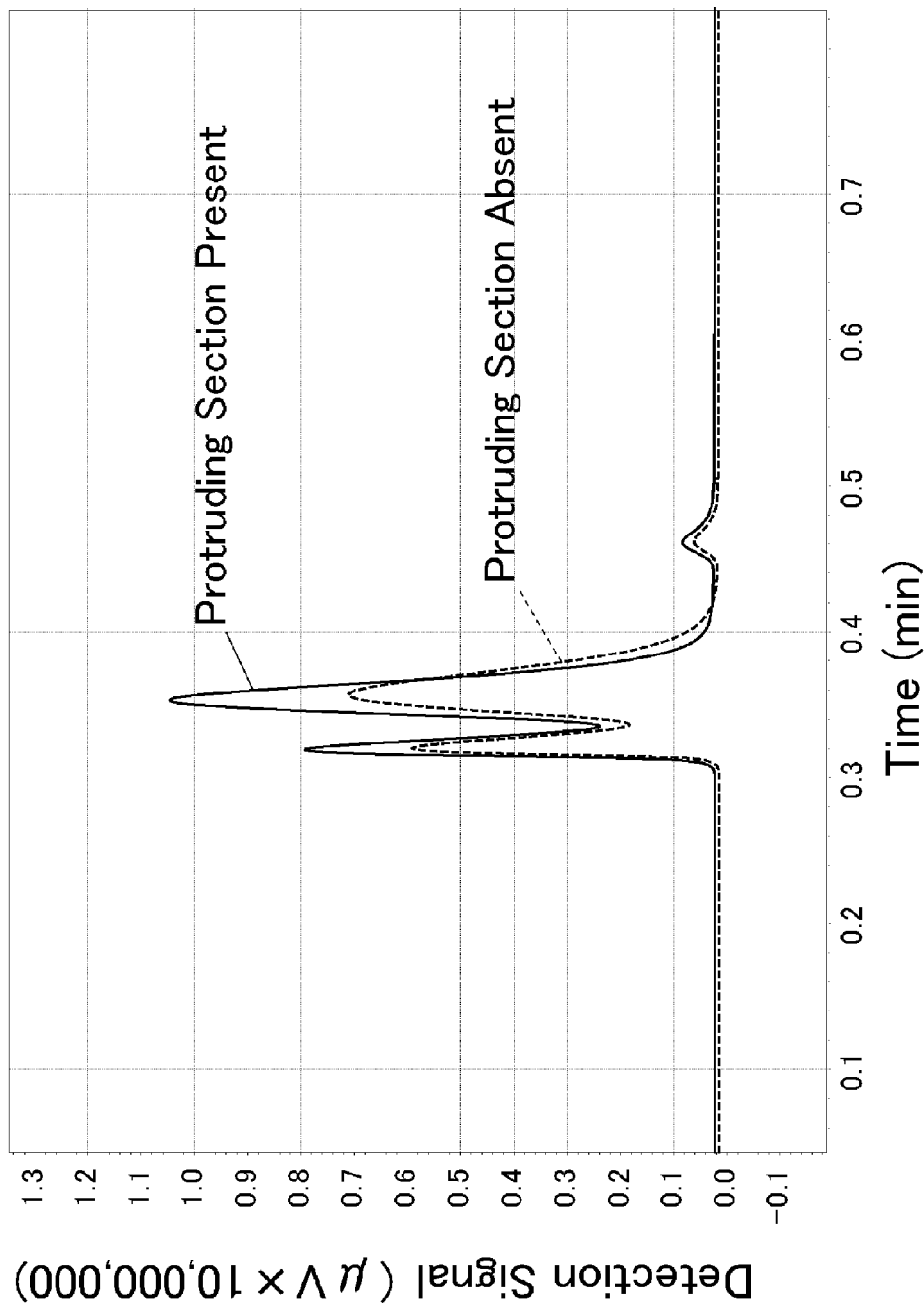

DISCHARGE IONIZATION CURRENT DETECTOR

BACKGROUND OF THE INVENTION

1. Field of the Invention

The present invention relates to a discharge ionization current detector to be used as a detector of an analysis device such as a gas chromatograph.

2. Description of the Related Art

As a detector capable of detecting, at high sensitivity, from inorganic substances to low boiling point organic compounds, there is a pulsed discharge ionization current detector (PDD). The discharge ionization current detector excites plasma generating gas such as the molecules of helium by high-voltage pulsed discharge, and ionizes a molecule to be analyzed by using optical energy generated at the time of the molecules returning from the excited state to the ground state. Then, a detection signal according to the amount of the molecule to be analyzed is obtained by detecting the ion current (see JPA 2010-060354).

Such a conventional discharge ionization current detector includes a plasma generating unit at its upper part, and a sample ionization/detection unit at its lower part. The plasma generating unit is provided as one section of a dielectric tube, such as a quartz tube, for example, through which the plasma generating gas, such as helium, flows. Three, upper, middle and lower, ring-shaped electrodes are attached to the outer circumference of the dielectric tube so as to encircle the outer circumference in the flow direction of the plasma generating gas. The part between the upper electrode and the lower electrode is the plasma generating unit. A high alternating voltage is applied to the middle electrode by a high voltage AC source, and the upper electrode and the lower electrode are grounded. The plasma generating gas is excited by dielectric barrier discharge occurring between the upper, middle and lower electrodes.

The sample ionization/detection unit includes a charging electrode and an ion current detecting electrode. A sample gas supply tube for supplying sample gas to the sample ionization/detection unit is connected to the sample ionization/detection unit on the other side from the plasma generating unit. A plasma generating gas injection port of the dielectric tube of the plasma generating unit and a sample gas injection port of the sample gas supply tube are arranged facing each other, and a gas exhaust port for exhausting gas to outside is provided therebetween.

With such a discharge ionization current detector, almost all of the amount of sample ion generated by the sample ionization unit is affected by the amount of excitation light from the plasma generating unit, and the amount of excitation light from the plasma generating unit is affected by the discharge state of the plasma generating unit. That is, when the discharge state of the plasma generating unit is changed, the amount of excitation light from the plasma generating unit is changed, thereby affecting the amount of sample ions generated by the sample ionization unit. Therefore, it is important to stabilize the discharge state of the plasma generating unit.

As one factor preventing stabilization of the discharge state of the plasma generating unit, entering of sample gas into the plasma generating unit can be cited. With a discharge ionization current detector as described above, when the amount of supply of sample gas from the sample gas supply tube increases, the sample gas sometimes enters the dielectric tube of the plasma generating unit and reaches the plasma generating unit. When the sample gas reaches the plasma generating unit, discharge becomes less likely to occur in the plasma generating unit, causing problems such as reduction in the detection sensitivity due to weakening of plasma intensity, or in the worst case, the plasma itself is extinguished and measurement itself is made impossible.

SUMMARY OF THE INVENTION

The present invention has its object to prevent entering of sample gas into a plasma generating unit, and to stabilize plasma intensity in the plasma generating unit.

A discharge ionization current detector according to the present invention includes a dielectric tube through which plasma generating gas flows, a plasma generating unit formed from one section of the dielectric tube in a flow direction of the plasma generating gas, a casing connected to a lower end portion, in the flow direction of the plasma generating gas, of the dielectric tube, a sample ionization unit provided inside the casing, and an ion current detection unit for detecting a sample component ionized by the sample ionization unit.

The plasma generating unit includes, in the section, a plurality of discharging electrodes attached on an outer circumferential surface of the dielectric tube so as to encircle an outer circumference of the dielectric tube, where the plurality of discharging electrodes are arranged, spaced from one another, along the flow direction of the plasma generating gas and where plasma is generated by generation of dielectric barrier discharge among the discharging electrodes.

The casing includes a connection portion to which a lower end portion, in the flow direction of the plasma generating gas, of the dielectric tube is to be connected, a space having an inner diameter larger than an outer diameter of the end portion of the dielectric tube, a sample gas inlet, provided at a position facing the connection portion, for introducing sample gas into the space, and an exhaust port for exhausting gas inside the space.

The lower end, in the flow direction of the plasma generating gas, of the dielectric tube protrudes into the space inside the casing.

The flow velocity of the plasma generating gas is low near a plasma generating gas injection port of the dielectric tube, compared to inside the dielectric tube, due to the influence of diffusion, allowing sample gas to easily enter the dielectric tube. Accordingly, the present invention has a lower end, in the flow direction of the plasma generating gas, of the dielectric tube protruding into the space inside the casing, causing the distance between the plasma generating gas injection port of the dielectric tube and the plasma generating unit to be longer compared to where one end of the dielectric tube does not protrude into the space inside the casing. This is because, if the distance between the plasma generating unit and the plasma generating gas injection port of the dielectric tube is short, the sample gas may reach the plasma generating unit.

With the discharge ionization current detector of the present invention, since the distance between the plasma generating gas injection port and the plasma generating unit is long, the sample gas does not easily reach the plasma generating unit, and generation of discharge can be stabilized and the intensity of plasma generated at the plasma generating unit can be stabilized.

BRIEF DESCRIPTION OF THE DRAWINGS

FIG. 3 is a graph showing a change over time in a detection signal for a case where one end of a dieletric tube is protruding into a space inside a casing and for a case where it is not protruding, measured under a different condition from FIG. 2.

DETAILED DESCRIPTION OF THE INVENTION

In a preferred embodiment of the present invention, the protruding length of one end of a dielectric tube in a casing is set to a length by which sample gas introduced into the casing, at a set flow amount of plasma generating gas and a set flow amount of sample gas, does not reach a plasma generating unit inside the dielectric tube. This stabilizes the generation of discharge, and the intensity of plasma generated in the plasma generating unit is stabilized.

Figure 1:
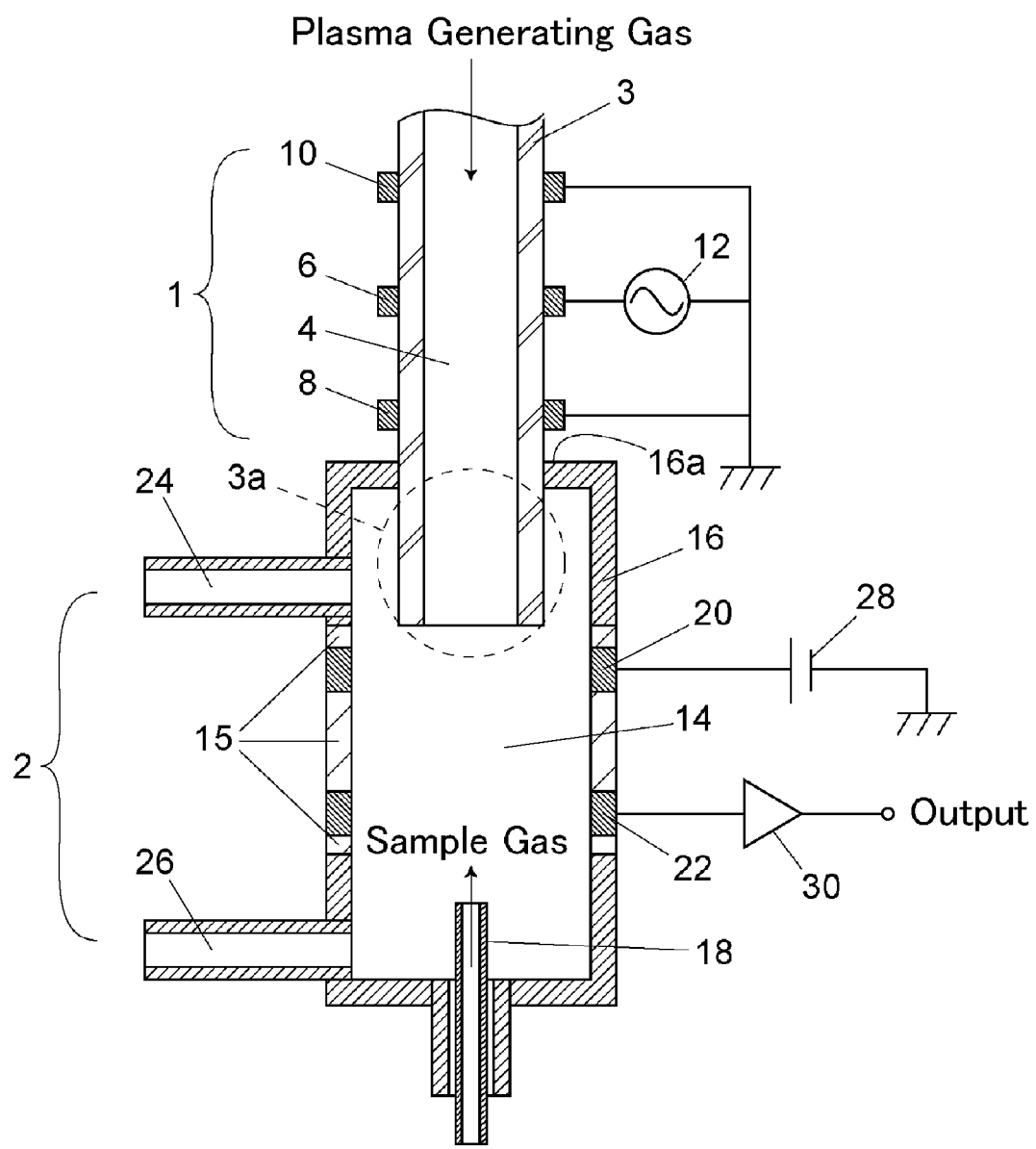
FIG. 1 is a cross-sectional view showing a structure of an embodiment of a discharge ionization current detector.

In the following, an embodiment of a discharge ionization current detector will be described with reference to FIG. 1.

The discharge ionization current detector includes a plasma generating unit 1 and a sample ionization/detection unit 2. The plasma generating unit 1 is provided as one section of a dielectric tube 3, such as a quartz tube, for example. Plasma generating gas, such as helium, flows through a passage 4 inside the dielectric tube 3 toward a casing 16 described later. Three ring-shaped electrodes 6, 8 and 10 are attached, spaced from one another and along the flow direction of the plasma generating gas flowing inside the dielectric tube 3, on the outer circumferential surface of the dielectric tube 3 so as to encircle the outer circumference of the dielectric tube 3. The plasma generating unit 1 is the section between the electrodes 6 and 10, and dielectric barrier discharge is generated between the electrode 6 and the electrodes 8 and 10 by application of a high alternating voltage on the electrode 6 by a high voltage AC source 12, and plasma generating gas is thereby excited. The electrodes 8 and 10 are grounded.

The sample ionization/detection unit 2 includes a casing 16, and a charging electrode 20 and an ion current detecting electrode 22 provided to the casing 16. The charging electrode 20 and the ion current detecting electrode 22 are ring-shaped electrodes, and the charging electrode 20 is provided on the plasma generating unit side than the ion current detecting electrode 22. The casing 16 is made of metal, and the charging electrode 20 and the ion current detecting electrode 22 are electrically separated from the casing 16 by an insulator 15.

The inner diameter of the casing 16 is larger than the dielectric tube 3. One end of the dielectric tube 3 is connected to a connection portion 16a at one end of the casing 16, and one end of a sample gas supply tube 18, which is a sample gas inlet for introducing sample gas into the casing 16, is connected to the other end, i.e. the opposite end, of the casing 16. A plasma generating gas injection port of the dielectric tube 3 and a sample gas injection port of the sample gas supply tube 18 are arranged facing each other. Gas exhaust ports 24 and 26 are provided at two positions on a side wall of the casing 16, and sample gas and plasma generating gas inside a space 14 of the casing 16 are exhausted from the gas exhaust ports 24 and 26.

Component molecules of a sample injected from the sample gas supply tube 18 into the space 14 inside the casing 16 are ionized by optical energy (excitation light) generated at the time of molecules of plasma generating gas excited by pulsed discharge in the plasma generating unit 1 returning to a ground state. The ionized component molecules are charged by the charging electrode 20 to which a voltage is applied by a DC source 28, and then, by exchanging electrons with the ion current detecting electrode 22, the amount of ionized sample components is input to a current amplifier 30 and is amplified by the current amplifier 30 and output as a detection signal.

One end of the dielectric tube 3 protrudes in the space 14 inside the casing 16. In the present embodiment, the length of a protruding portion 3a of the dielectric tube 3 is about 10 mm, for example, the inner diameter of the dielectric tube 3 is 2 mm, for example, and the inner diameter of the casing 16 is 13 mm, for example. Due to the presence of the protruding portion 3a of the dielectric tube 3, the distance between the plasma generating gas injection port of the dielectric tube 3 and the plasma generating unit 1 is longer compared to a conventional product.

The flow velocity of the plasma generating gas at the plasma generating gas injection port of the dielectric tube 3 is lower than the flow velocity of the plasma generating gas in the passage 4 inside the dielectric tube 3 due to the influence of diffusion, and thus, sample gas injected from the sample gas supply tube 18 easily enters the dielectric tube 3. When the sample gas reaches the plasma generating unit 1, this affects generation of dielectric barrier discharge at the plasma generating unit 1. It is conceivable to move the plasma generating unit 1 away from the plasma generating gas injection port by moving the positions of the electrodes 6, 8 and 10 away from the casing 16, but this will reduce the intensity of excitation light applied by the plasma generating unit 1 on the sample gas in the casing 16, causing a problem that the ionization efficiency of a sample component is reduced and the sensitivity is reduced.

Accordingly, by causing one end of the dielectric tube 3 to protrude into the space 14 and providing, between the plasma generating unit 1 and the plasma generating gas injection port, a section where the flow velocity of the plasma generating gas is increased, the sample gas is prevented from easily reaching the plasma generating unit 1.

The length of the protruding portion 3a is determined by the flow amount of plasma generating gas and the flow amount of sample gas, and is set such that the sample gas does not reach the plasma generating unit 1 inside the dielectric tube 3. When using a discharge ionization current detector having a protruding portion 3a of a certain length, the flow amount of plasma generating gas and the flow amount of sample gas are adjusted such that the sample gas does not reach the plasma generating unit 1 inside the dielectric tube 3.

With the protruding portion 3a provided, the flow amount of plasma generating gas necessary for preventing the sample gas from reaching the plasma generating unit 1 is reduced compared to a case where the protruding portion 3a is not provided, and there is an advantage that the consumption amount of the plasma generating gas can be reduced.

Figure 2:
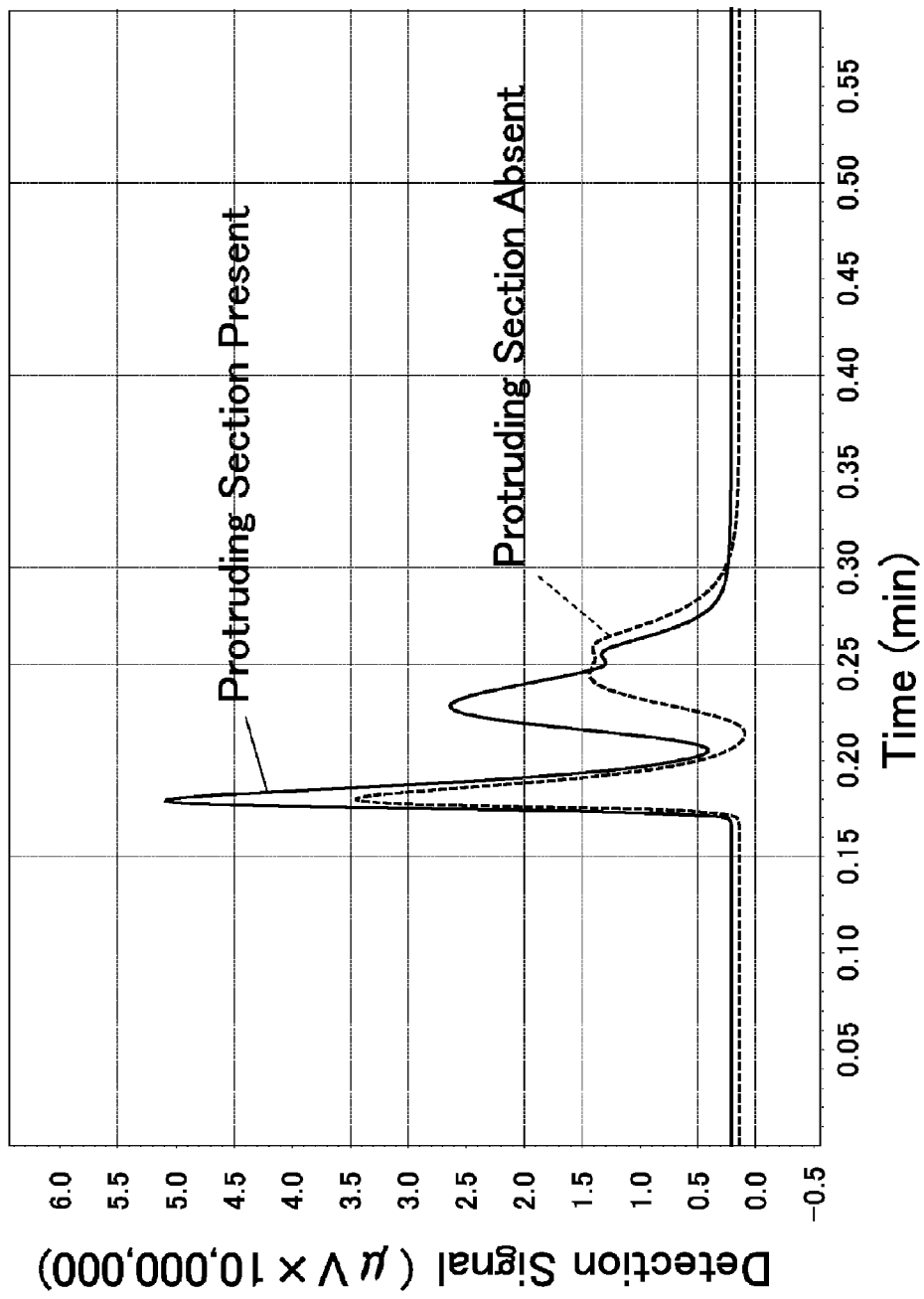
FIG. 2 is a graph showing a change over time in a detection signal for a case where one end of a dielectric tube protrudes into a space inside a casing and for a case where it does not protrude.

FIGS. 2 and 3 both show data (measurement data) on the change over time in a detection signal for a case where one end of the dielectric tube (the quartz tube) 3 protrudes into the space 14 inside the casing 16 and for a case where it does not protrude. Additionally, in the measurement of FIG. 2, sample gas (carrier gas) is supplied to the space 14 in the casing 16 under a condition of 20 ml per minute, and in the measurement of FIG. 3, the sample gas (the carrier gas) is supplied to the space 14 in the casing 16 under a condition of 10 ml per minute.

It can be seen, by the data in FIGS. 2 and 3, that the peak is more significant and the detection sensitivity is increased when one end of the dielectric tube 3 protrudes into the space 14 in the casing 16 than where it does not protrude. It is assumed that protrusion of one end of the dielectric tube 3 into the space 14 in the casing 16 restricts entering of sample gas into the plasma generating unit 1, thereby increasing the efficiency of generation of plasma and the efficiency of generation of excitation light applied to the component gas of the sample. With the increase in the efficiency of generation of excitation light, the efficiency of ionization of a component molecule of the sample in the space 14 in the casing 16 is increased, and as a result, a molecular ion detection signal is enhanced.

The invention claimed is:

1. A discharge ionization current detector comprising:
   a dielectric tube through which plasma generating gas flows;
   a plasma generating unit formed from one section of the dielectric tube in a flow direction of the plasma generating gas, the plasma generating unit including, in the section, a plurality of discharging electrodes attached on an outer circumferential surface of the dielectric tube so as to encircle an outer circumference of the dielectric tube, wherein the plurality of discharging electrodes are arranged, spaced from one another, along the flow direction of the plasma generating gas and wherein plasma is generated by generation of dielectric barrier discharge among the discharging electrodes;
   a casing including a connection portion to which a lower end portion, in the flow direction of the plasma generating gas, of the dielectric tube is connected, a space having an inner diameter larger than an outer diameter of the end portion of the dielectric tube, a sample gas inlet, provided at a position facing the connection portion, for introducing sample gas into the space, and an exhaust port for exhausting gas inside the space;
   a sample ionization unit provided inside the casing; and
   an ion current detection unit for detecting a sample component ionized by the sample ionization unit,
   wherein the lower end, in the flow direction of the plasma generating gas, of the dielectric tube protrudes into the space inside the casing.

2. The discharge ionization current detector according to claim 1, wherein a protruding length of the end portion of the dielectric tube inside the casing is set to a length by which the sample gas introduced into the casing at a set flow amount of plasma generating gas and a set flow amount of sample gas does not reach the plasma generating unit in the dielectric tube.

3. The discharge ionization current detector according to claim 2, wherein the dielectric tube is of cylindrical form, and the casing is of cylindrical form with an inner diameter larger than an outer diameter of the dielectric tube.

4. The discharge ionization current detector according to claim 1, wherein the dielectric tube protrudes into the space inside the casing by about 10 mm.

* * * * *